United States Patent
Kunkler (10) Patent No.: US 9,168,358 B1
(45) Date of Patent: Oct. 27, 2015

(54) DEVICE THAT HOLDS AN INTRAOSSEOUS INFUSION SYSTEM IN PLACE ON AN INDIVIDUAL'S LEG

(71) Applicant: David Kunkler, Logan, OH (US)

(72) Inventor: David Kunkler, Logan, OH (US)

(*) Notice: Subject to any disclaimer, the term of this patent is extended or adjusted under 35 U.S.C. 154(b) by 0 days.

(21) Appl. No.: 14/259,944

(22) Filed: Apr. 23, 2014

Related U.S. Application Data (60) Provisional application No. 61/816,319, filed on Apr. 26, 2013.

(51) Int. Cl.
*A61M 5/32* (2006.01)
*A61M 25/02* (2006.01)

(52) U.S. Cl.
CPC ........ *A61M 25/02* (2013.01); *A61M 2025/0206* (2013.01); *A61M 2210/02* (2013.01)

(58) Field of Classification Search
CPC ............. A61M 5/002; A61M 2005/3205; A61M 2005/321; A61M 2005/3212; A61M 2005/3213; A61M 5/158; A61M 2025/026; A61M 25/02; A61M 2025/0206; A61B 5/150748; A61B 5/15074

USPC .............. 604/179, 180, 178, 307, 890.1, 174
See application file for complete search history.

(56) References Cited

U.S. PATENT DOCUMENTS

2009/0281565 A1* 11/2009 McNeese ...................... 606/201
2011/0282291 A1* 11/2011 Ciccone ......................... 604/178

* cited by examiner

*Primary Examiner* — Emily Schmidt
*Assistant Examiner* — Hamza Darb
(74) *Attorney, Agent, or Firm* — Jerry Semer (57) ABSTRACT

The invention protects an intraosseous infusion system from being bumped or displaced. The device is a strap and an implement that holds the intraosseous infusion system. The implement is comprised of two pieces. A U shaped piece that has an opening that holds the intraosseous infusion device. The second piece when snapped into place encircles the intraosseous infusion device to securely hold the intraosseous infusion device in place. To use the invention, the invention is place over the intraosseous infusion device placed in the patient's leg and the strap is tightened around the patient's leg. Then the second piece is pushed around the intraosseous infusion device to hold it securely in place.

7 Claims, 13 Drawing Sheets

DEVICE THAT HOLDS AN INTRAOSSEOUS INFUSION SYSTEM IN PLACE ON AN INDIVIDUAL'S LEG

This application is a continuation in part of prior application No. 61/816,319 filed Apr. 26, 2013.

FIELD OF THE INVENTION

This invention relates to the type of devices that are used in intraosseous infusion and more particularly to devices that protects an intraosseous infusion needle from being disturbed or dislodged.

BACKGROUND OF THE INVENTION

Emergency medical services have recently obtained a new weapon in providing immediate vascular access to the central circulation. This weapon is a small IO device for an IV that is drilled in the tibia just below the kneecap. The inventor, an emergency medical technician, has helped to place many of these I/O devices within individuals. Although the placement of the I/O device is easy, the devices can be accidentally knocked out easily. To solve this problem the inventor has devised a device that holds the needle in place and protects it when inadvertently bumped or knocked.

The new small IO has been created by Vidacare and is called EZ-IO intraosseous infusion system. The small IO is comprised of a hollow needle and a cap (catheter hub) that is designed to take a catheter from an IV or a needle for infusing medicine or liquids. The device is used when the patient has poor peripheral vasculature and for whose whom vascular access can be challenging. It is a quick and easy solution at the scene of an accident or on the battlefield where action must be immediate and the injured individual may not be in an ideal position. The EZ-IO is easy to place however it is also come out easily. To overcome this problem the inventor has developed a device that will hold the EZ-IO in place on the leg. The feature that enables the inventor's device to hold the EZ-IO is a device that constricts around the EZ-IO and a strap that encircle the leg to hold the constricting device and the EZ-IO in place on the leg.

SUMMARY OF THE INVENTION

The invention is a device that is designed to hold an intraosseous infusion system in place when the intraosseous infusion system is implanted in an individual's leg. The invention protects the intraosseous infusion system in place from being bumped and displaced by the environment. The device is a strap and an implement that holds the intraosseous infusion system in place when the intraosseous infusion system is placed in an individual's leg. In the preferred embodiment the strap can be tighten around the individual's leg. On each end of the implement an attachment means attaches a strap to the implement. The implement is a constriction device that constricts around the intraosseous infusion device after the intraosseous infusion device is places within the individual's tibia.

In the preferred embodiment the constriction device is comprised of two pieces. The first piece is a U shaped piece that has an opening in its center of a sufficient size that the intraosseous infusion device will fit. The U shape piece is of sufficient height to hold the intraosseous infusion device in place within a patient's leg. At the ends of the constriction device are openings to which the strap is attached. Extending downward from the opening in the U shaped piece is a partial cylindrical extension. The partial cylindrical extension envelops the intraosseous infusion device. It fits snugly around the intraosseous infusion device to hold the intraosseous infusion device in place. A slot extends from the opening in the center of the U shaped piece to the edge of the U-shaped piece. The partial cylindrical extension also has an opening in its front that corresponds to the slot in the U-shaped piece. Opposite the slot on the back end of the U-shaped piece are two L shaped overhangs.

The second piece has a ridge that extends from its top. The second piece is rectangular and thin. It has a large slit that runs down its center starting near its top. The top portion of the slit is small. The middle portion extends outward and is circular in shape. The diameter of the circular shape is slightly smaller than the diameter of the intraosseous infusion device. The bottom portion of the slit is nearly as large as the circular portion and extends to the bottom of the second piece. The slit produces two arms that extend downward from the top of the second piece. These two arms are slightly flexible. The thickness and the width of the second piece will enable it to fit between and under the two L shaped overhangs.

Another embodiment the constriction device is comprised of two pieces. The first piece is a U shaped piece that has an opening in its center of a sufficient size that the intraosseous infusion device will fit through. The U shape piece is of sufficient height that it fits over the intraosseous infusion device. At the ends of the constriction device are openings to which the strap is attached.

On one side of the opening in the center of the device is a set of gears that partially encircles the side of the opening. On the other side of the opening in the center of the constriction device is another smaller opening. This smaller opening is designed to take an axle from the second piece, the pivotal piece. At one end of the pivotal piece is a set of gears that are designed to intermesh with the gears on the U shaped piece. On the same end of the pivotal piece as the gears, the pivotal piece has a V-shaped opening. The V-shaped opening is of sufficient size that its edges will make contact with the intraosseous infusion device when placed around the intraosseous infusion device. In the center of the pivotal piece is a cylindrical column that is designed to snap into the smaller opening on the U-shaped piece. This column forms an axle and allows the pivotal piece to pivot. At the end of the pivotal piece opposite the end with the gears is a flap. This flap is designed such that when an individual puts pressure on the flap the pivotal piece will pivot.

To use the first embodiment, the intraosseous infusion device is placed in the patient's leg. Then one that takes the constriction device with the strap and places it on the patient's leg. The strap loosely encircles the patient's leg. The constriction device and the strap are pulled up the leg to a position over the intraosseous infusion device. The constriction device is then a lowered over the intraosseous infusion device and the intraosseous infusion device is placed through the opening in the center of the U shaped piece. The strap than is tightened on the patient's leg.

The second piece is than place under the L shaped overhangs and pushed forward towards the intraosseous infusion device. The slot between the two arms of the second piece is of sufficient size that when it makes contact with the intraosseous infusion device it flexes outward and the arms begins moving around the intraosseous infusion device. As the second piece is moved forward the middle circular portion of the slot snaps in place around the intraosseous infusion device. The arms of the slot have sufficient flexibility to hold the intraosseous infusion device in place.

To use the second embodiment, the intraosseous infusion device is placed in the patient's leg. Then one that takes the constriction device with the strap and places it on the patient's leg. The strap loosely encircles the patient's leg. The constriction device and the strap are pulled up the leg to a position over the intraosseous infusion device. The constriction device is then a lowered over the intraosseous infusion device and the intraosseous infusion device is placed through the opening in the center of the U shaped piece. The strap than is tightened on the patient's leg.

Then one puts pressure on the flap on the pivotal piece causing the pivotal piece to pivot and forcing the edges of the V-shaped cutout in the pivotal piece to make contact with the intraosseous infusion device. When the pivotal piece pivots it ratchets the gears on the top of the pivotal piece and the U shaped piece together. The ratcheting of the gears holds the pivotal piece's V-shaped cutout against the sides of the intraosseous infusion device. The friction between the edges of the V-shaped cutout and the intraosseous infusion device is sufficient to hold the intraosseous infusion device securely in place even if the patient's leg is bumped or moved or the intraosseous infusion device is bumped.

DETAILED DESCRIPTION OF THE PREFERRED EMBODIMENT

Figure 1:
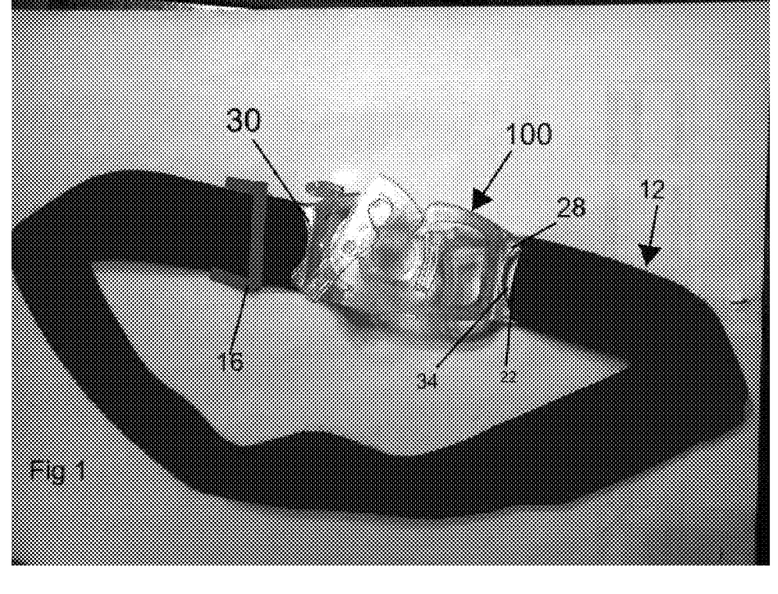
FIG. 1 is a perspective view of the invention
Figure 2:
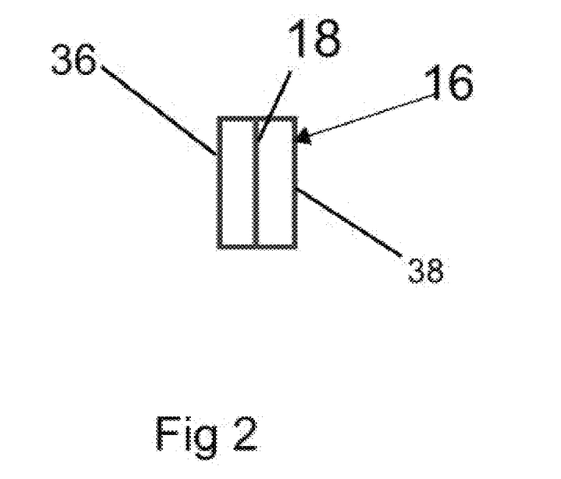
FIG. 2 is a top view of the triglide slider 16.

FIG. 1 is a perspective view of one embodiment of invention. The invention has two parts. Part one is the constriction device 10 or 100. Attached to both ends of the constriction device 10 or 100 is a strap 12. Strap 12 is designed to encircle the patient's leg in which the intraosseous infusion device 14 is to be placed. On the strap 12 is a means for tightening and loosing the strap 12. In the preferred embodiment the strap 12 is tighten and loosen by a triglide slider. FIG. 2 shows the triglide slider 16. Triglide slider 16 has a front bar 36 and a rear bar 38. The triglide slider 16 has an additional bar 18 extending across its center. An end of the strap 12 is attached the additional bar 18. On the two ends 24 and 26 of the constriction device 10 or 100 are D shaped loops 28 and 30. The back of the D shaped loops 28 and 30 attach to the constriction device 10 or 100. The front of the D is a bar that extends outward to form openings 32 and 34 at each end of the constriction device 10 or 100. The openings 32 and 34 are of sufficient size that the strap 12 can pass through. End 22 of strap 12, the end not attached to the bar 18 is ran through openings 32 on constriction device 10 or 100. End 22 is then run back to the triglide slider 16. End 22 is loped under the front bar 36 and over the additional bar 18. End 22 of strap 12 continues on under rear bar 38 and is finally is attached to D shaped loop 28 on the constriction device 10. End 22 is attached to constriction device 10 by running the end 22 of strap 12 through opening 34 and attaching the end 22 of strap 12 to strap 12.

The strap 12 is loosened around a patient's leg by moving the triglide slider 16 towards the constriction device 10. The strap and 12 is tightened by pulling the triglide slider 16 away from constriction device 10 or 100.

Figure 3:
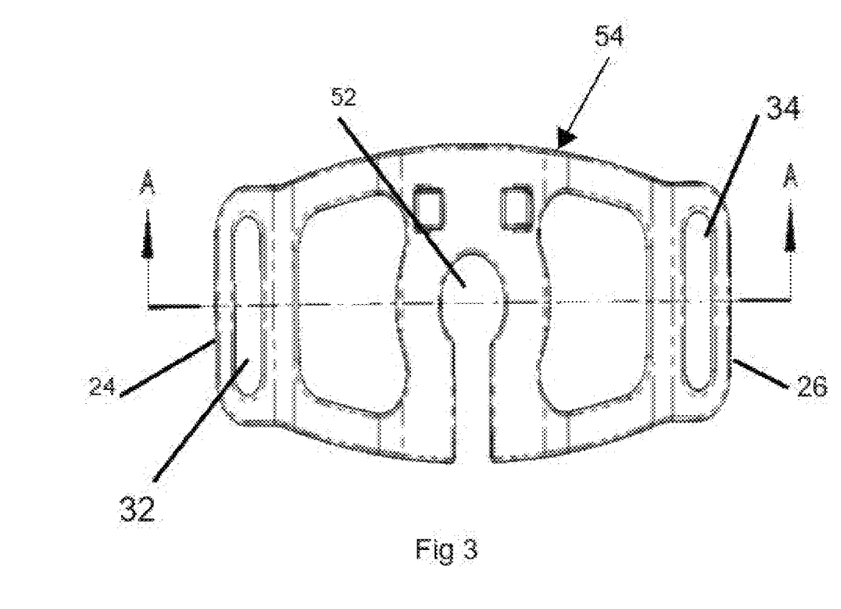
FIG. 3 the top view of the U shaped piece 54 of the constriction device 10 of the first embodiment of the invention.
Figure 4:
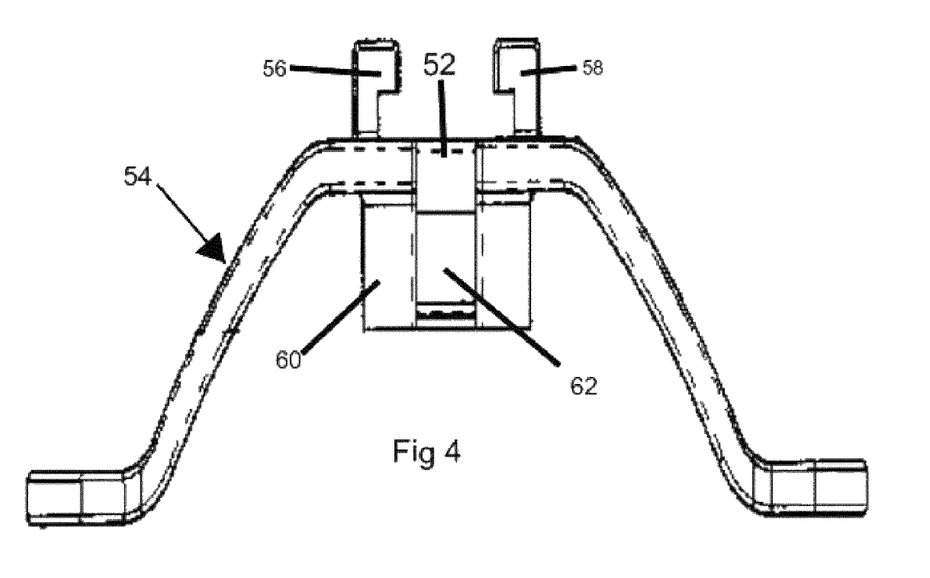
FIG. 4 is a side view of the U shaped piece 54 of the constricting device 10 of the first embodiment of the invention.
Figure 4A:
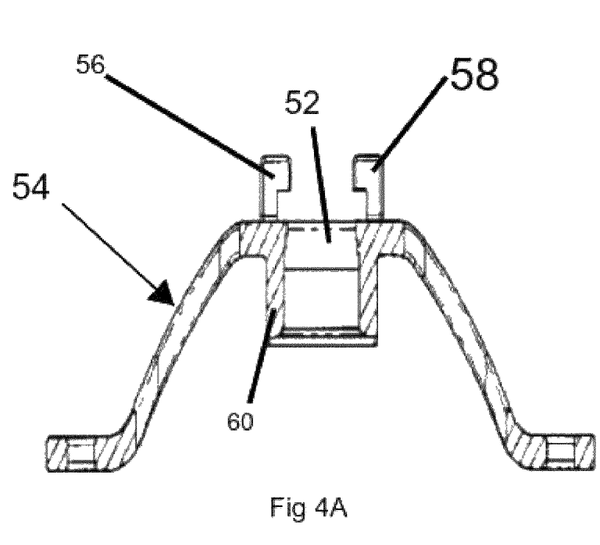
FIG. 4A is a sectional view of the U shaped piece 54 of the constricting device 10 of the first embodiment of the invention along line A-A of FIG. 3.
Figure 5:
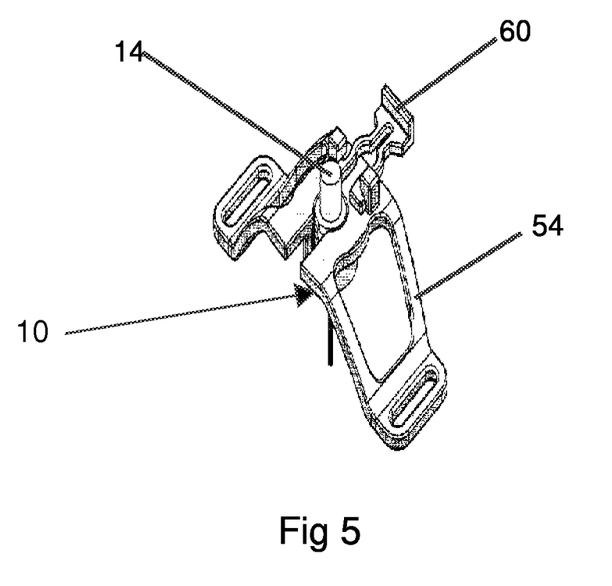
FIG. 5 is a perspective view of the constriction device of one embodiment of the invention with the intraosseous infusion device in place before the second pieces snaps around the intraosseous infusion device.
Figure 6:
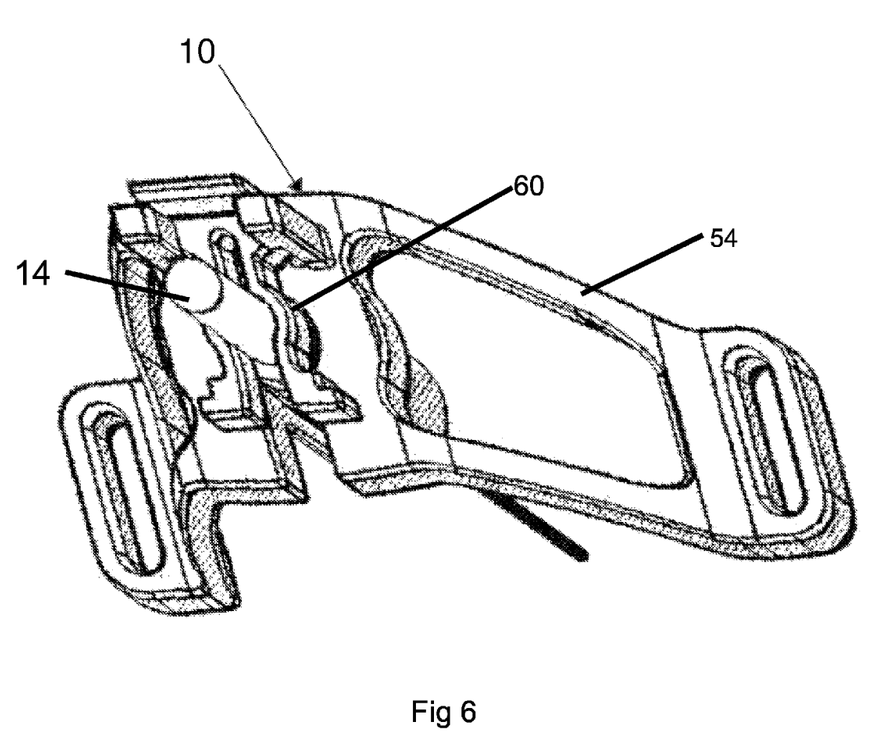
FIG. 6 is a perspective view of the constriction device of one embodiment of the invention with the intraosseous infusion device in place after the second pieces snaps around the intraosseous infusion device to hold it securely in place.

The constriction device 10 is made of two different pieces. FIGS. 1, 5 and 6 show the two pieces when they are attached. FIG. 3 shows the top view of the U shaped piece 54. At the top of the "U" in the center of the U shaped piece 54 is a center opening 52. Center opening 52 is of a sufficient size that the intraosseous infusion device 14 will fit through center opening 52 as shown in FIGS. 5 and 6. FIG. 4 is a side view of U shaped piece 54 of the constriction device 10. FIG. 4A is a sectional view of the U shaped piece 54 along line A-A of FIG. 3. These figures show that constriction device 10 has a U shaped configuration. The U-shaped configuration is of a sufficient height that it will hold the intraosseous infusion device 14 when placed in the leg of the patient securely on that leg. FIGS. 5 and 6 shows the constriction device 10 with the intraosseous infusion device 14 place within.

FIG. 4 shows the U shaped piece 54 of the constriction device 10. On the ends 24 and 26 of the U shaped piece 54 are openings 32 and 34. The strap 12 fits through these openings 32 and 34. At the top of the U-shaped piece 54 in its center is center opening 52. Center opening 52 is of sufficient size that the intraosseous infusion device 14 will fit through center opening 52.

Extending downward from the center opening 52 in the U shaped piece 54 is a partial cylindrical extension 60. The partial cylindrical extension 60 envelops the intraosseous infusion device 14. It fits snugly around the intraosseous infusion device 14 to hold the intraosseous infusion device 14 in place. A slot 62 extends from the center opening 52 in the U shaped piece 54 to the edge of the U-shaped piece 54. The partial cylindrical extension 60 also has a front opening 64 in its front that corresponds to the slot 62 on the top of the U-shaped piece 54. Opposite the slot 62 on the back end of the U-shaped piece 54 are two L shaped overhangs 56 and 58.

Figure 3A:
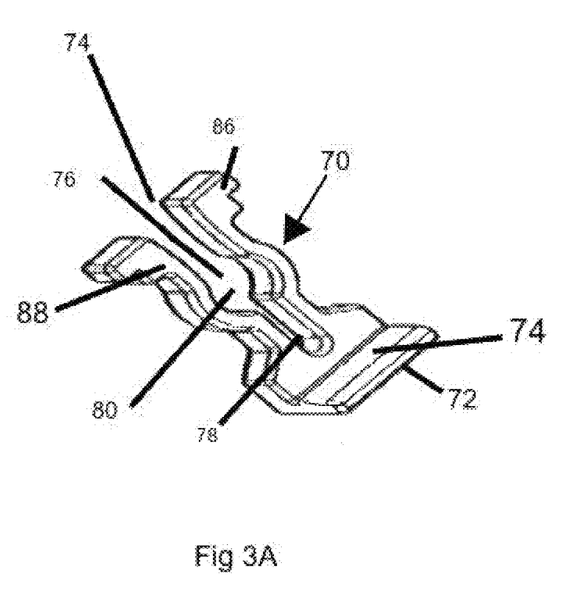
FIG. 3A is a perspective view of the second piece 60 of the constricting device 10 of the first embodiment of the invention.

The second piece 70 shown in FIG. 3A has a ridge 74 that extends from its top 72. The second piece 70 is rectangular and thin. It has a large slit 76 that runs down its center starting near its top 72. The top portion 78 of the slit 76 is small. The middle portion 70 extends outward and is circular in shape. The diameter of the circular shape middle portion 70 is slightly smaller than the diameter of the intraosseous infusion device 14. The bottom portion 72 of the slit is nearly as large as the circular shape middle portion 80 and extends to the bottom 74 of the second piece 70. The slit 76 produces two arms 86 and 88 that extend downward from the top of the second piece 60. These two arms 86 and 88 are slightly flexible. The thickness and the width of the second piece 60 will enable it to fit between and under the two L shaped overhangs 56 and 58.

FIG. 1 is a perspective view of a second embodiment of invention. The second embodiment of the invention just like the first has two parts 12 and 154. Part one is the constriction device 100. Attached to both ends of the constriction device 100 is a strap 12. Strap 12 works exactly the same in this embodiment as it did in the previous embodiment. Strap 12 of this embodiment is designed to encircle the patient's leg in which the intraosseous infusion device 14 is to be placed. In this embodiment strap 12's means for tightening and loosing is a triglide slider 16 that works exactly as in the previous embodiment.

Figure 7:
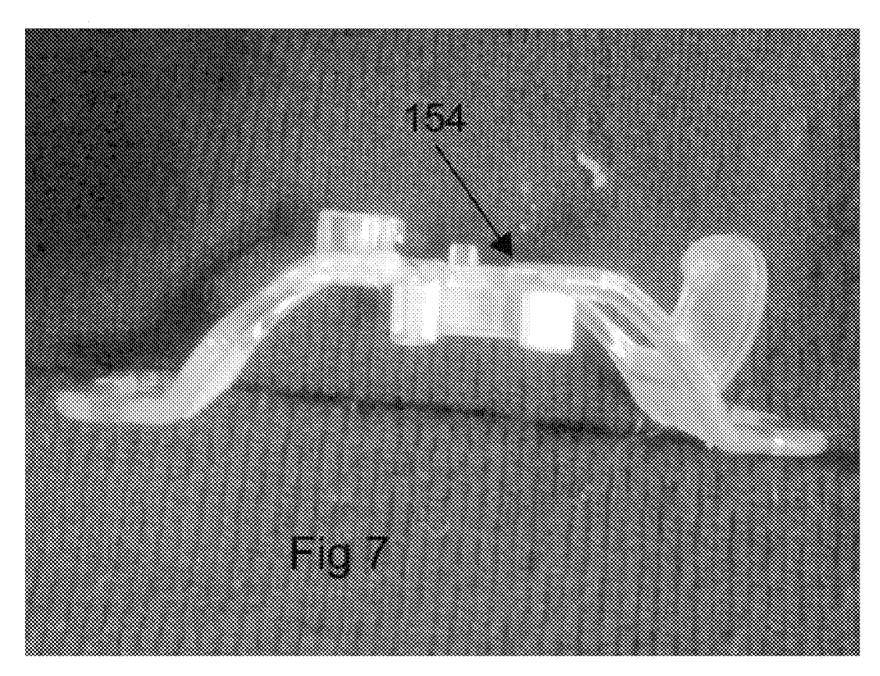
FIG. 7 is a side view of the U shaped piece 154 of the constricting device 100 of the second embodiment of the invention.
Figure 8:
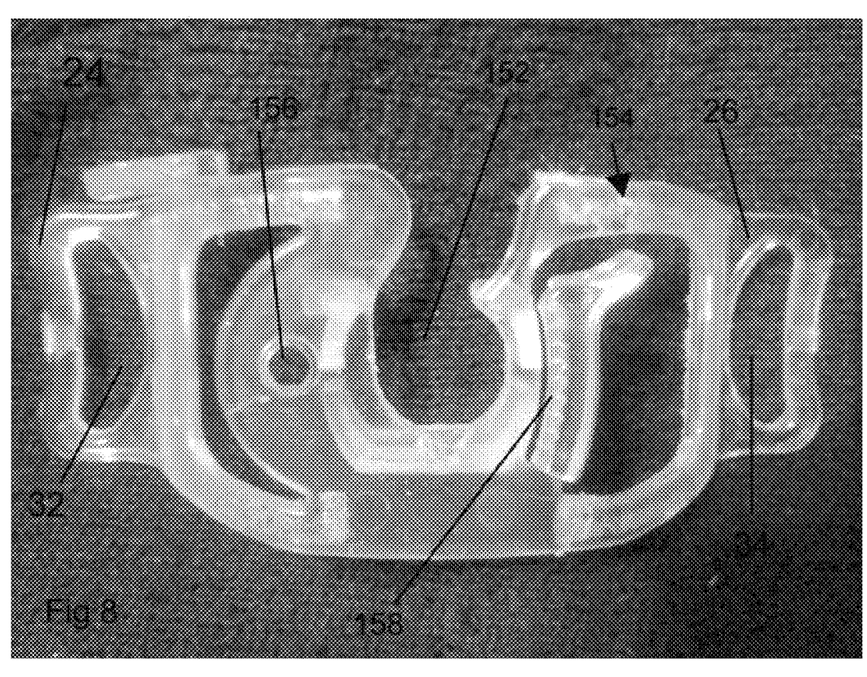
FIG. 8 is a top view of the U shaped piece 154 of the constricting device 100 of the second embodiment of the invention.
Figure 11:
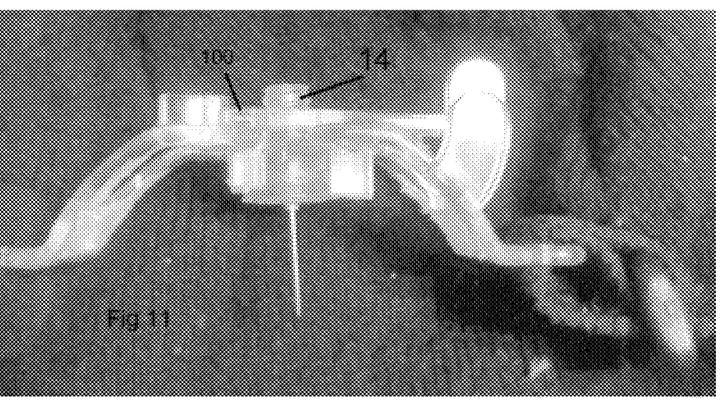
FIG. 11 is a side view of the U shaped piece 154 with the intraosseous infusion device 14.

FIG. 7 is a side view of U shaped piece 154 of the constriction device 100. This figure shows that constriction device 100 has a U shaped configuration. The U-shaped configuration is of a sufficient height that it will hold the intraosseous infusion device 14 when placed in the leg of the patient securely on that leg. FIG. 11 shows the constriction device 100 with the intraosseous infusion device 14 place within. FIG. 8 shows the top view of the U shaped piece 154. At the top of the "U" in the center of the U shaped piece 154 is a center opening 152. On one side of opening 152 is another smaller opening 156. On the opposite side of opening 152 is a set of gears 158. This set of gears 158 is semicircular and curves around opening 152.

Figure 9:
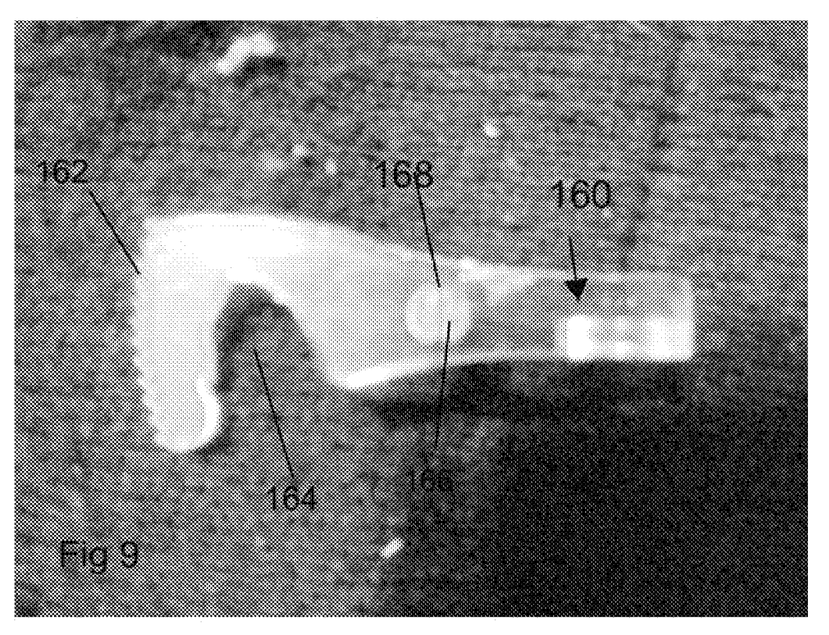
FIG. 9 is a top view of the pivoting piece 160 of the constriction device 100.
Figure 10:
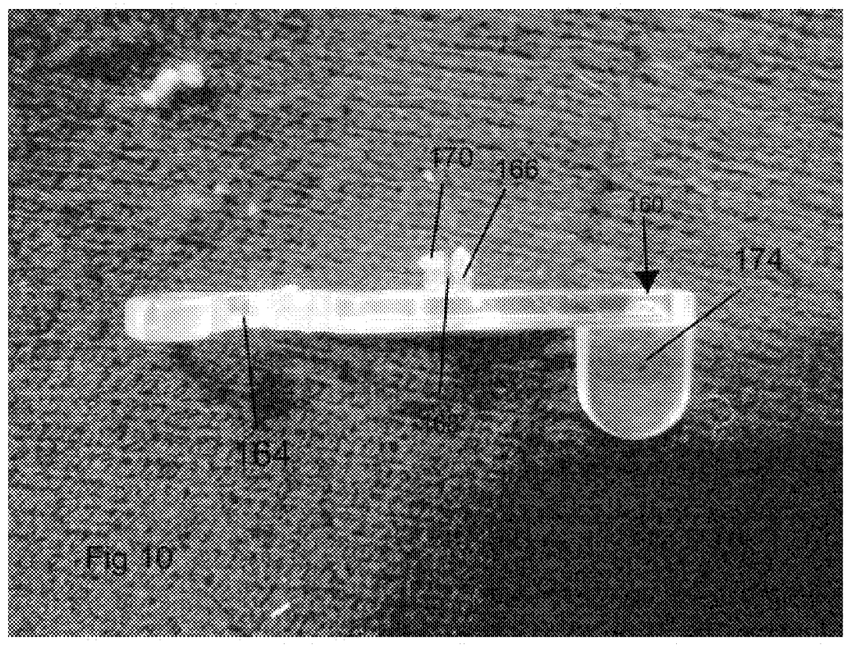
FIG. 10 is a side view of the pivoting piece 160 of the constriction device 100.

FIGS. 9 and 10 show the pivoting piece 160 of the constricting device 100. On one end of pivoting device 160 is a set of gears 162. This set of gears 162 is designed to interlock with the set of gears 158 of the U-shaped piece 154. When the pivoting piece 160 is placed upon the U shaped piece 154 the 2 sets of gears 158 and 162 mash and one set of gears 158 or 162 forms a ratchet for the other set of gears 158 or 162. On the same end of the pivoting piece 160 but closer to the center of the pivoting piece 160 is a V shaped cutout 164. The V shaped cutouts 164 is of sufficient size that it can fit around the intraosseous infusion device 14. In the center of the pivotal piece 160 protrudes a circular column 166. The circular column 166 has slits 168 down its sides. At the top of circular column 160 is a ridge 170 that protrudes perpendicular and outward from column 166. Ridge 170 has a slanted top. Column 160 with its slanted top ridge 170 is designed to snap into smaller opening 156 in the U-shaped piece 154. Column 166 is designed to form an axle within opening 156. The axle formed by column 166 enables pivotal piece 60 to pivot. At the end of the pivotal piece 160 opposite the end with the gears 62 a flap 174 extends upward from the pivotal piece 160. This flap 174 when pressure is placed upon it will cause the pivotal piece 160 when it is in place on the constriction device 100 to pivot.

To the use either of the embodiments of the invention the intraosseous infusion device 14 is placed in the patient's leg. Then one takes the constriction device 10 or 100 with the strap 12 and places it on the patient's leg. The strap 12 loosely in circles the patient's leg. The constricting device 10 or 100 and strap 12 are pulled up the leg to a position over top the intraosseous infusion device 14. The constricting device 10 or 100 is then lowered over the intraosseous infusion device 14 and the intraosseous infusion device 14 is placed through opening 52 or 152. The strap 12 is then tightened upon the patient's leg.

In the first embodiment one than puts pressure on the ridge 64 of the second piece 60 pushing it under the L shaped overhangs 56 and 58 and against and around the intraosseous infusion device 14 until the arms 76 and 78 of the second piece 60 snap around the intraosseous infusion device 14 and hold it security within the middle portion 70 of the slit 66. Even if the patient's leg is bumped or moved or the intraosseous infusion device 14 is bumped, the intraosseous infusion device will remain in place.

Once one has placed the second embodiment of the constriction device 100 on the leg over the intraosseous infusion device 14, one puts pressure on the flap 174 causing the pivotal piece 160 to pivot and forcing the edges of the V shaped cutout 164 to make contact with the intraosseous infusion device 14. When the pivotal piece 162 pivots it ratchets gears 158 and 162 together. This ratcheting of gears 158 and 162 holds pivotal piece's 160 V-shape cut out 164 against the sides of the intraosseous infusion device 14. The friction between the edges of the V-shaped cutout 164 and the intraosseous infusion device 14 is sufficient to hold the intraosseous infusion device 14 securely in place even if the patient's leg is bumped or moved or the intraosseous infusion device 14 is bumped.

Changes and modifications in the specificity described embodiments can be carried out without departing from the scope of the invention that is intended to limited only by the scope of the appending claims.

I claim:

1. A device to hold and protect an intraosseous infusion device comprising:
   a. an adjustable strap; and,
   b. an U shaped piece with two ends that is attached to the adjustable strap at each end: and,
   c. the U shaped piece has an opening with a perimeter in a center of the U shaped piece that the intraosseous infusion device can pass through; and,
   d. a constricting piece that is attached to the U shaped piece that is able to constrict around the intraosseous infusion device when the intraosseous infusion device is placed through the opening in the U shaped piece,
   e. wherein the strap with the U shaped piece and the constricting piece are place around an individual's appendage and moved into position over the intraosseous infusion device, and the U shaped piece is placed over intraosseous infusion device allowing the intraosseous infusion device to pass through the opening in the U shaped piece and then the constricting piece is moved to constrict around the intraosseous infusion device,
   f. the constricting piece is rectangular and has a large slit that runs down a center of the constricting piece starting near a top of the constricting piece and continuing to a bottom of the constricting piece running along a longest dimension of the constricting piece forming two arms and a middle portion of the slit extend outward and is circular in shape with the middle portion of the slit diameter being slightly smaller than the diameter of the intraosseous infusion device and a bottom portion of the slit extends outward as the slit moves towards the bottom of the constricting piece forming a keyhole shape with the circular middle portion and the two arms are slightly flexible.

2. The device to hold and protect an intraosseous infusion device as in claim 1 wherein:
   a. the U shaped piece has two L shaped overhangs behind the opening, and,
   b. the constricting piece fits underneath and between the L shaped overhangs.

3. The device to hold and protect an intraosseous infusion device as in claim 2 wherein:
   a. the constricting piece has a ridge that extends outward from the top of the constricting piece at a right angle,
   b. wherein the constricting piece is moved to constrict around the intraosseous infusion device by pushing on the ridge and moving the constricting piece around the intraosseous infusion device.

4. The device to hold and protect an intraosseous infusion device as in claim 3 wherein:
   a. the U shaped piece has a slot that extends forward from the opening to a front edge of the U shaped piece.

5. The device to hold and protect an intraosseous infusion device as in claim 4 wherein:
   a. the U shaped piece has a cylindrical extension that extends downward from the opening and has an inner perimeter that matches the perimeter of the opening and has a slit in its front that corresponds to the slot in the U-shaped piece.

6. The device to hold and protect an intraosseous infusion device as in claim 1 wherein:
   a. the U shaped piece has a slot that extends through the U shaped piece and extends forward from the opening to the U shaped piece's front edge.

7. The device to hold and protect an intraosseous infusion device as in claim 6 wherein:
   a. the U shaped piece has a cylindrical extension that extends downward from the opening and has an inner perimeter that matches the perimeter of the opening and has a slit in a front of the cylindrical extension that corresponds to the slot in the U-shaped piece.

\* \* \* \* \*